(12) United States Patent
Levijoki

(10) Patent No.: US 7,279,479 B2
(45) Date of Patent: Oct. 9, 2007

(54) METHOD FOR THE TREATMENT OF HEART FAILURE

(75) Inventor: Jouko Levijoki, Helsinki (FI)

(73) Assignee: Orion Corporation (FI)

( * ) Notice: Subject to any disclaimer, the term of this patent is extended or adjusted under 35 U.S.C. 154(b) by 167 days.

(21) Appl. No.: 10/467,459

(22) PCT Filed: Feb. 8, 2002

(86) PCT No.: PCT/FI02/00099

§ 371 (c)(1),
(2), (4) Date: Dec. 2, 2003

(87) PCT Pub. No.: WO02/062342

PCT Pub. Date: Aug. 15, 2002

(65) Prior Publication Data

US 2004/0092523 A1    May 13, 2004

(30) Foreign Application Priority Data

Feb. 8, 2001   (FI) ................................. 20010233

(51) Int. Cl.
*A61K 31/50*   (2006.01)
*A61K 33/42*   (2006.01)
*A61K 33/14*   (2006.01)
*A61K 33/06*   (2006.01)

(52) U.S. Cl. ...................... 514/247; 424/602; 424/678; 424/682

(58) Field of Classification Search ................. 514/247
See application file for complete search history.

(56) References Cited

U.S. PATENT DOCUMENTS

| | | | |
|---|---|---|---|
| 4,529,602 A * | 7/1985 | Wada et al. ................. | 514/569 |
| 4,745,130 A | 5/1988 | Wurtman | |
| 4,971,982 A * | 11/1990 | Attwood et al. ............. | 514/337 |
| 5,120,738 A * | 6/1992 | Ikawa et al. ........... | 514/255.01 |
| 5,424,428 A | 6/1995 | Nore et al. | |
| 5,512,571 A | 4/1996 | Nore et al. | |
| 5,569,657 A | 10/1996 | Nore et al. | |
| 5,998,458 A * | 12/1999 | Bristow ....................... | 514/392 |
| 6,030,943 A * | 2/2000 | Crumb et al. .................. | 514/9 |
| 6,323,226 B1 * | 11/2001 | Delgado et al. ............. | 514/343 |
| 6,355,269 B1 * | 3/2002 | Backman et al. ........... | 424/464 |
| 6,448,248 B1 | 9/2002 | Amberg et al. | |
| 6,531,458 B1 * | 3/2003 | Larma et al. .................. | 514/54 |
| 6,730,673 B1 * | 5/2004 | Backstrom et al. ......... | 514/247 |

FOREIGN PATENT DOCUMENTS

| | | |
|---|---|---|
| EP | 0 411 766 A1 | 2/1991 |
| EP | 0 565 546 B1 | 3/1995 |
| WO | WO92/12135 | 7/1992 |
| WO | WO93/21921 | 11/1993 |
| WO | WO98/27070 | 6/1998 |
| WO | WO99/16443 * | 4/1999 |
| WO | WO99/55337 * | 11/1999 |
| WO | WO99/66912 | 12/1999 |

OTHER PUBLICATIONS

Handbook of Pharmaceutical Excipients, published 1986 by American Pharmaceutical Association (DC), pp. 26-33.*
Cecil Textbook of Medicine, Goldman et al. (editors), 21$^{st}$ Edition, vol. 1, published 2000, pp. 215-225.*
Handbook of Pharmaceutical Excipients, published by the American Pharmaceutical Association, 1986, pp. 36-40 and 44.*
F. Guideri et al., "Calcium infusion induces myocardial ischaemia in patients with coronary artery disease by a mechanism possibly adenosine mediated", European Heart Journal, vol. 15, pp. 1158-1163 (1984).
Nicolai Gruhn et al., "Coronary Vasorelaxant Effect of Levosimendan, a New Inodilator with Calcium-Sensitizing Properties", Journal of Cardiovascular Pharmacology, vol. 31, pp. 741-749 (1998).
Heimo Haikala et al., "The role of cAMP- and cGMP-dependent protein kinases in the cardiac actions of the new calcium sensitizer, levosimendan", Cardiovascular Research, vol. 34, pp. 536-546 (1997).
Herwig Köppel et al., "Minimal Effects of Levosimendan on Coronary Artery Smooth Muscle Tone", Cardiovascular Drugs and Therapy vol. 13, pp. 357-358 (1999).
Derwent Abstract of WO 98/27070 (2003).
J. Lilleberg et al., "Effects of a new calcium sensitizer, levosimendan, on haemodynamics, coronary blood flow and myocardial substrate utilization early after coronary artery bypass grafting," European Heart Journal (1998) 19: 660-668.
Stig Sundberg et al., "Hemodynamic and Neurohumoral Effects of Levosimendan, a New Calcium Sensitizer, at Rest and During Exercise in Healthy Men," Am. J. Cardiol (1995) 75:1061-1066.
Esa-Pekka Sandell et al., "Pharmacokinetics of Levosimendan in Healthy Volunteers and Patients with Congestive Heart Failure," Journal of Cardiovascular Pharmacology, 26 (Suppl. 1): S57-S62 (1995).
J. Lilleberg et al., "Dose-Range Study of a New Calcium Sensitizer, Levosimendan, in Patients with left Ventricular Dysfunction", Journal of Cardiovascular Pharmacology, 26 (Suppl. 1): S63-S69 (1995).
Lynette R. Moser et al., "The use of calcium salts in the prevention and management of verapamil-induced hypotension", American Chemical Society (2002)—Abstract 133:159.
William G. Hughes et al., "Should Calcium Be Used in Cardiac Arrest?," The American Journal of Medicine, (1986) 81:285-296.

* cited by examiner

*Primary Examiner*—Raymond J. Henley, III
(74) *Attorney, Agent, or Firm*—Finnegan, Henderson, Farabow, Garrett & Dunner, LLP

(57) ABSTRACT

A combination therapy for the treatment of heart failure, particularly acute heart failure, comprises administering a combination of levosimendan or a pharmaceutically acceptable salt thereof and a calcium ion source and/or an intracellular calcium increasing agent to a patient. The combination shows a synergistic effect even at doses having no effect if administered alone.

6 Claims, 1 Drawing Sheet

METHOD FOR THE TREATMENT OF HEART FAILURE

This application is a U.S. national stage filing of PCT International Application No. PCT/FI02/00099, filed on Feb. 8, 2002. This application also claims the benefit of priority to Finnish patent application no. 20010233, filed on Feb. 8, 2001.

TECHNICAL FIELD

The present invention relates to a method for the treatment of heart failure, in particular acute heart failure, by administering a synergistic combination of levosimendan and a calcium ion source and/or an intracellular calcium increasing agent to a patient in need of such treatment.

BACKGROUND OF THE INVENTION

Levosimendan, which is the (−)-enantiomer of [[4-(1,4,5,6-tetrahydro-4-methyl-6-oxo-3-pyridazinyl)phenyl]hydrazono]propanedinitrile, and the method for its preparation is described in EP 565546 B1. Levosimendan is potent in the treatment of heart failure and has significant calcium dependent binding to troponin. Levosimendan is represented by the formula:

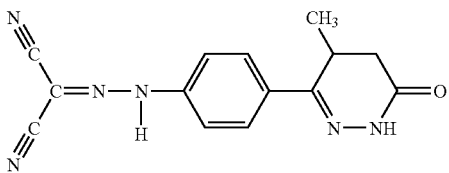

The hemodynamic effects of levosimendan in man are described in Sundberg, S. et al., Am. J. Cardiol., 1995; 75: 1061-1066 and in Lilleberg, J. et al., J. Cardiovasc. Pharmacol., 26(Suppl. 1), S63-S69, 1995. Pharmacokinetics of levosimendan in man after i.v. and oral dosing is described in Sandell, E.-P. et al., J. Cardiovasc. Pharmacol., 26(Suppl.1), S57-S62, 1995. The use of levosimendan in the treatment of myocardial ischemia is described in WO 93/21921. The use of levosimendan in the treatment of pulmonary hypertension is described in WO 99/66912. Clinical studies have confirmed the beneficial effects of levosimendan in congestive heart failure patients.

Intravenous administration of calcium salts has been used clinically to raise the ionized calcium content in blood e.g. in the treatment of cardiac arrest. On the other hand, it is known that high intracellular calcium level may have deleterious effect in some processes of cellular injury (Hughes W. G. and Ruedy, J. R, "Should calcium be used in cardiac arrest?", The Americal Journal of Medicine, 81, 285-296, 1986).

SUMMARY OF THE INVENTION

It has now been found that a concomitant administration of levosimendan and a calcium ion source, even at doses having no effect if administered alone, had a marked synergistic effect on the survival in acute heart failure induced by verapamil or diltiazem. Moreover, the synergistic effects are also seen in the concomitant administration of levosimendan with various agents capable of increasing intracellular calcium level in the cardiac cells. Therefore, the combination of levosimendan and a calcium ion source and/or an intracellular calcium increasing agent is particularly useful for the treatment of heart failure, especially acute heart failure.

Thus, in one aspect the present invention provides a method for the treatment of heart failure, said method comprising administering to a patient in need thereof as active ingredients levosimendan or a pharmaceutically acceptable salt thereof and a calcium ion source and/or an intracellular calcium increasing agent.

In another aspect the invention provides a medical product comprising, separately or together, as active ingredients levosimendan or a pharmaceutically acceptable salt thereof and a calcium ion source and/or an intracellular calcium increasing agent as a combined preparation.

In another aspect invention provides a pharmaceutical composition comprising as active ingredients levosimendan or a pharmaceutically acceptable salt thereof and a calcium ion source and/or an intracellular calcium increasing agent.

In still another aspect the invention provides the use of levosimendan or a pharmaceutically acceptable salt thereof and a calcium ion source and/or an intracellular calcium increasing agent as active ingredients in the manufacture of a combined preparation for simultaneous, separate or sequential administration.

DETAILED DESCRIPTION

Figure 1:
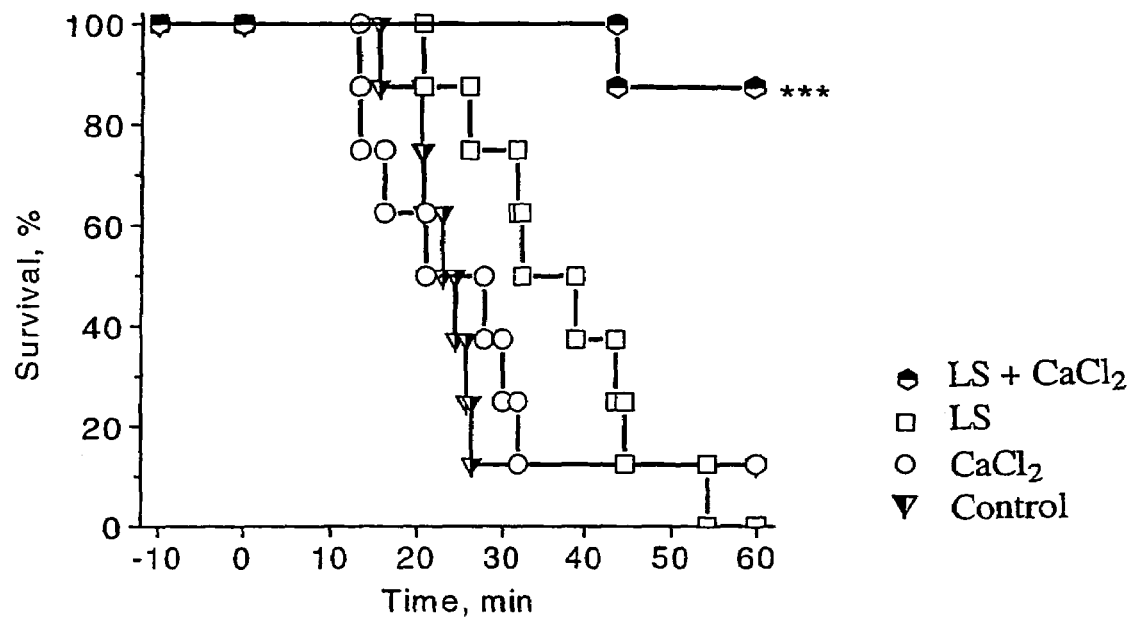
FIG. 1 shows the effect of levosimendan, calcium chloride and their combination on the survival of anesthetized guinea-pigs intoxicated with verapamil. At zero time, the intoxication was started with an intravenous bolus injection of verapamil and immediately continued with a 4-min infusion. The total dose of verapamil was 2.0 mg/kg. Control animals were treated with saline. All treatments were started one minute after the end of the verapamil infusion. *$p<0.05$, $p<0.01$, *$p<0.001$ vs. control (Kaplan-Meier survival analysis followed by the logrank test).

The method of the invention comprises a combination therapy for the treatment of heart failure, particularly acute heart failure, by administering to a patient in need thereof as active ingredients levosimendan or a pharmaceutically acceptable salt thereof and a calcium ion source and/or an intracellular calcium increasing agent. The active ingredients may be administered simultaneously, separately or sequentially. In particular, the method comprises administering to a patient an amount of active ingredients which is effective to improve the survival and/or the hemodynamic function of a patient suffering from heart failure. Preferably, the method comprises administering to a patient a synergistically effective amount of the combination. In particular, the synergistic effect makes possible to administer a low dose of the combination so as to minimize the undesirable effects of the active ingredients. The administration routes of the active ingredients include, but are not limited to, enteral, e.g. oral or rectal, or parenteral, e.g. intravenous, intramuscular, intraperitoneal or transdermal. In the treatment of acute heart failure, the active ingredients are preferably administered parenterally, intravenous route being particularly preferred.

According to the invention, levosimendan may be administered e.g. intravenously using an infusion rate which is from about 0.005 to 10 µg/kg/min, preferably from about 0.01 to 0.5 µg/kg/min, typically as low as from about 0.02 to 0.2 µg/kg/min. For an intravenous bolus a suitable dose is in the range from about 1 to 200 µg/kg, preferably from about 2 to 100 µg/kg, typically as low as from about 5 to 10 µg/kg. For the treatment of acute heart failure an intravenous bolus followed by continuous infusion may be needed.

According to the invention, the suggested daily dose of levosimendan is in general from about 0.05 to 10 mg, preferably from 0.1 to 5 mg, more preferably from 0.2 to 2 mg, depending on the age, body weight and condition of the patient. The effective amount of levosimendan to be administered to a subject depends upon the condition to be treated, the route of administration, age, weight and the condition of the patient.

The calcium source may be any pharmaceutically acceptable compound capable to donor calcium ions and having sufficient water-solubility. Suitable calcium sources are inorganic and organic calcium salts known in the art. Suitable inorganic calcium salts include calcium chloride, calcium phosphate, calcium biphosphate, calcium carbonate and others. Suitable organic calcium salts include calcium gluconate, calcium gluceptate, calcium malate, monocalcium citrate, tricalcium dicitrate, calcium glycerophosphate and others. Calcium chloride is preferred.

According to the invention, calcium source may be administered e.g. intravenously using an infusion rate which is (as calcium ions) from about 0.01 to 5 mg/kg/min, preferably from about 0.02 to 1 mg/kg/min, typically as low as from about 0.05 to 0.5 mg/kg/min. For an intravenous bolus a suitable dose (as calcium ions) is in the range from about 0.05 to 50 mg/kg, preferably from about 0.1 to 10 mg/kg, typically as low as from about 0.2 to 5 mg/kg. Similar doses can be used in oral administration. A suggested daily dose of the calcium source (as calcium ions) is from about 10 to 3000 mg, preferably from about 20 to 500 mg, depending upon the condition to be treated, the route of administration, age, weight and the condition of the patient.

The term "intracellular calcium increasing agent" as used herein means any pharmaceutically acceptable agent capable of increasing intracellular calcium levels, particularly in the cardiac cells. Such agent include, but are not limited to, agonists of the adrenergic beta-receptors, particularly beta-1 receptors, such as dobutamine or xamoterol; phosphodiesterase inhibitors, particularly phosphodiesterase isoenzyme III inhibitors, such as milrinone, anrinone or enoximone; inhibitors of the sodium/potassium ATPase, such as digoxin; openers of L-type calcium channels; openers of sodium channels; and blockers of potassium channels.

The intracellular calcium increasing agent is administered using a dose which is effective to increase intracellular calcium in cardiac cells. For example, an intracellular calcium increasing agent may be administered using the conventional dosage ranges for these agents. The range will, of course, vary depending on the agent employed. However, it is preferred to use intracellular calcium increasing agents in low doses, i.e. in doses which are sufficient to produce a slight increase in the intracellular calcium level but which are sufficiently low such that significant effects which are not desired in the treatment of heart failure are not produced.

The active ingredients can be formulated into pharmaceutical dosage forms suitable for the treatment of acute heart failure using the principles known in the art. They are given to a patient as such or preferably in combination with suitable pharmaceutical excipients in the form of tablets, dragees, capsules, suppositories, emulsions, suspensions or solutions whereby the contents of the active compound in the formulation is from about 0.5 to 100% per weight. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds, release controlling components and other ingredients normally used in this field of technology may be also used.

Pharmaceutical compositions in the form of intravenous solutions are preferred.

The active ingredients may be formulated in the same pharmaceutical formulation. Alternatively, the active ingredients are formulated as separate pharmaceutical dosage forms. The combination of the pharmaceutical dosage forms may be packaged as a single medical product or kit for use in the method of the invention, optionally together with a package insert instructing to the correct use of the medical product.

Pharmaceutical formulations suitable for intravenous administration of levosimendan such as injection or infusion formulation, comprise sterile isotonic solutions of levosimendan and vehicle, preferably aqueous solutions. Typically an intravenous infusion solution comprises from about 0.01 to 0.1 mg/ml of levosimendan. The pharmaceutical formulation may be also in the form of an intravenous infusion concentrate to be diluted with an aqueous vehicle before use. Such concentrate may comprise as a vehicle a pharmaceutically acceptable organic solvent such as dehydrated ethanol.

Calcium source may be included in the levosimendan infusion solution or concentrate or may be formulated separately as described above. Typically an intravenous infusion solution comprises from about 1 to 100 mg/ml of calcium ions.

Similarly, the intracellular calcium increasing agent may be included in the levosimendan infusion solution or may be formulated separately as described above using the principles well kcnown in the art.

One preferred embodiment of the invention is a medical product comprising, separately or together, as active ingredients levosimendan or a pharmaceutically acceptable salt thereof and a calcium ion source as a combined preparation.

Another preferred embodiment of the invention is a medical product comprising, separately or together, as active ingredients levosimendan or a pharmaceutically acceptable salt thereof and an intracellular calcium increasing agent as a combined preparation.

Salts of levosimendan may be prepared by known methods. Pharmaceutically acceptable salts are useful as active medicaments, however, preferred salts are the salts with alkali or alkaline earth metals.

EXAMPLES

Pharmaceutical example.

Example 1

Concentrate Solution for Intravenous Infusion

| (a) levosimendan | 2.5 mg/ml |
|---|---|
| (b) Kollidon PF12 | 10 mg/ml |
| (c) citric acid | 2 mg/ml |
| (d) dehydrated ethanol | ad 1 ml (785 mg) |

The concentrate solution was prepared by dissolving citric acid, Kollidon PF121 and levosimendan to dehydrated ethanol in the sterilized preparation vessel under stirring. The resulting bulk solution was filtered through a sterile filter (0.22 µm). The sterile filtered bulk solution was then aseptically filled into 8 ml and 10 ml injection vials (with 5 ml and 10 ml filling volumes) and closed with rubber closures.

The concentrate solution for intravenous infusion is diluted with an aqueous vehicle before use. Typically the concentrate solution is diluted with aqueous isotonic vehicles, such as 5% glucose solution or 0.9% NaCl solution so as to obtain an aqueous intravenous solution, wherein the amount of levosimendan is generally within the range of about 0.001-1.0 mg/ml, preferably about 0.01-0.1 mg/ml.

Experiments 120 spontaneously breathing guinea-pigs (Dunkin Hartley, weighing 470±5 grams, mean±SEM) were anesthetised with isoflurane. The left ventricular and brachial arterial pressures were measured. The carotid artery was surgically exposed in order to introduce a pressure transducer into the left ventricle. A fluid-filled polyethylene cannula was inserted into the brachial artery and connected to another pressure transducer for recording of arterial pressure. The pressure signals were amplified, digitized and sampled. After stabilization, the baseline hemodynamics were recorded for ten minutes before induction of verapamil or diltiazem intoxication.

Verapamil and diltiazem intoxications were induced in guinea-pigs by a short-lasting intravenous infusion of these drugs into the brachial vein. The infusions containing 10.0 mg/mL of verapamil or 2.26 mg/mL of diltiazem were administered at the rate of 0.5 mL/kg/min over a four minute period. The total doses of these drugs were 2.0 and 4.5 mg/kg, respectively.

Guinea-pigs were randomized to be intoxicated with either verapamil or diltiazem and thereafter both intoxication groups were further randomized into groups: control (saline), low dose of levosimendan, low dose of calcium chloride, and low dose of levosimendan combined with the low dose of calcium chloride. All treatments were administered as a bolus injection followed by an infusion into the brachial vein. Both control groups received saline (0.9% sodium chloride solution) as a bolus injection (1.0 mL/kg) followed by an infusion at the rate of 50 µL/kg/min. Levosimendan was initially administered as an intravenous bolus injection at the dose of 8.4 µg/kg. The bolus injection was immediately followed by infusion of 0.14 µg/kg/min, given over one hour. Calcium chloride was given as an intravenous bolus injection of 10 mg/kg, immediately followed by an infusion of 0.5 mg/kg/min. Guinea-pigs were also treated with a combination of low dose of levosimendan and low dose of calcium chloride using doses as described above. All these treatments were commenced one minute after administration of calcium channel blocker and the infusions were continued throughout the follow-up period of 60 minutes or until death ensued. At the end of experiments, the surviving animals were sacrificed by an overdose of pentobarbital.

Figure 2:
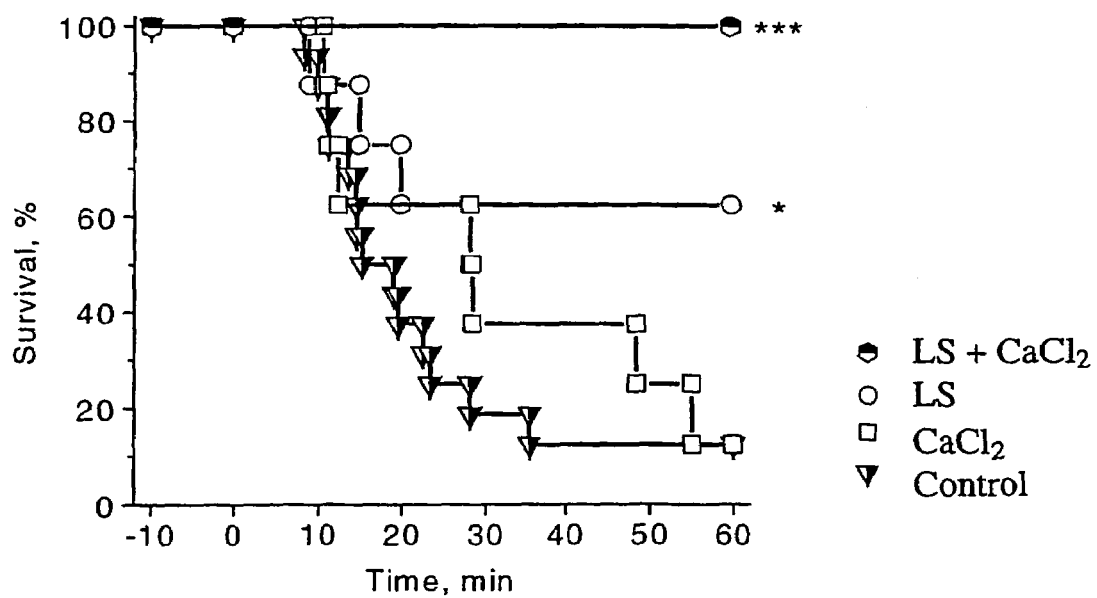
FIG. 2 shows the effect of levosimendan, calcium chloride and their combination on the survival of anesthetized guinea-pigs intoxicated with diltiazem. At zero time, the intoxication was started with an intravenous bolus injection of diltiazem and immediately continued with a 4-min infusion. The total dose of diltiazem was 4.5 mg/kg. Control animals were treated with saline. All treatments were started one minute after the end of the diltiazem infusion. *$p<0.05$, $p<0.01$, *$p<0.001$ vs. control (Kaplan-Meier survival analysis followed by the logrank test).

The results are shown in FIGS. 1 (verapamil group) and 2 (diltiazem group). At 60 minutes after verapamil or diltiazem intoxication began, only 13% of guinea-pigs were alive in control groups. Low dose of levosimendan (LS) did not improve the survival in veraparnil intoxicated animals. (FIG. 1). In diltiazem intoxicated animals, low dose levosimendan (LS) improved the survival rate to 63% (FIG. 2).

The low dose of calcium chloride ($CaCl_2$) did not affect the survival rate either in verapamil or diltiazem intoxicated guinea-pigs. Although the low dose of levosimendan (LS) and calcium chloride ($CaCl_2$) alone had no effect on survival rate in verapamil intoxicated guinea-pigs, the combination of these treatments had a marked synergistic effect (88% survival, FIG. 1). In diltiazem intoxication, the combination of levosimendan (LS) with calcium chloride ($CaCl_2$) also improved survival rate more than levosimendan (LS) or calcium chloride ($CaCl_2$) treatment alone (FIG. 2).

The invention claimed is:

1. A method for the treatment of heart failure, said method comprising simultaneous, separate or sequential administration intravenously to a patient in need thereof as active ingredients levosimendan or a pharmaceutically acceptable salt thereof and a calcium ion source and/or an intracellular calcium increasing agent, wherein the intracellular calcium increasing agent does not increase intracellular calcium levels solely by donating calcium ions.

2. A method according to claim 1, wherein the calcium ion source is a pharmaceutically acceptable inorganic or organic calcium salt.

3. A method according to claim 2, wherein the inorganic calcium salt is calcium chloride, calcium phosphate, calcium biphosphate or calcium carbonate.

4. A method according to claim 2, wherein the organic calcium salt is calcium gluconate, calcium gluceptate, calcium malate, monocalcium citrate, tricalcium dicitrate or calcium glycerophosphate.

5. A method according to claim 2, wherein the pharmaceutically acceptable inorganic or organic calcium salt is administered to provide a daily dose of calcium ions from 20 to 500 mg.

6. A method according to claim 1, wherein the intracellular calcium increasing agent is an adrenergic beta-receptor agonist, a phosphodiesterase inhibitor, a sodium/potassium ATPase inhibitor, a L-type calcium channel opener, a sodium channel opener, or a potassium channel blocker.

* * * * *